(12) United States Patent
Wheeler et al.

(10) Patent No.: US 12,350,437 B2
(45) Date of Patent: Jul. 8, 2025

(54) RESPIRATORY DEVICE

(71) Applicant: Engineered Medical Systems, Inc., Indianapolis, IN (US)

(72) Inventors: Bradley Allen Wheeler, Martinsville, IN (US); Jessica Mae Zinnecker, Indianapolis, IN (US); James DuCanto, Wauwatosa, WI (US)

(73) Assignee: Engineered Medical Systems, Inc., Indianapolis, IN (US)

( * ) Notice: Subject to any disclaimer, the term of this patent is extended or adjusted under 35 U.S.C. 154(b) by 1180 days.

(21) Appl. No.: 17/176,423

(22) Filed: Feb. 16, 2021

(65) Prior Publication Data
US 2022/0257900 A1     Aug. 18, 2022

(51) Int. Cl.
| | |
|---|---|
| *A61M 16/20* | (2006.01) |
| *A61M 16/06* | (2006.01) |
| *A61M 16/10* | (2006.01) |
| *A61M 16/12* | (2006.01) |

(52) U.S. Cl.
CPC ...... *A61M 16/201* (2014.02); *A61M 16/0672* (2014.02); *A61M 16/1015* (2014.02); *A61M 16/12* (2013.01)

(58) Field of Classification Search
CPC .................................. A62B 9/02; A61M 39/22
See application file for complete search history.

(56) References Cited

U.S. PATENT DOCUMENTS

| | | | | |
|---|---|---|---|---|
| 3,598,134 | A * | 8/1971 | Ollivier | A61M 16/12 137/7 |
| 3,727,627 | A * | 4/1973 | Bird | A61M 16/20 137/100 |
| 3,762,439 | A * | 10/1973 | Heath | A61M 16/107 137/893 |
| 4,141,354 | A * | 2/1979 | Ismach | A61M 16/021 128/204.26 |
| 4,886,055 | A | 12/1989 | Hoppough | |
| 5,452,714 | A | 9/1995 | Anderson et al. | |
| 5,755,220 | A * | 5/1998 | Ando | A61M 16/12 128/205.24 |
| 6,186,477 | B1 | 3/2001 | MCombs et al. | |
| 6,378,520 | B1 | 4/2002 | Davenport | |
| 8,181,650 | B2 | 5/2012 | Nelson et al. | |
| 8,365,727 | B2 | 2/2013 | Dunsmore et al. | |

(Continued)

*Primary Examiner* — Valerie L Woodward
(74) *Attorney, Agent, or Firm* — Woodard, Emhardt, Henry, Reeves & Wagner, LLP

(57) ABSTRACT

A valve for use with a compressed breathable gas source having a valve adapted to: (a) be disposed upstream of a patient delivery device and (b) control at least a portion of a breathable gas source upstream of the patient delivery device and the source including both: (i) a compressed breathable gas source and (ii) a second gas source. The valve includes a first rotatable body. The first rotatable body adjusts, upon rotation thereof a cross-sectional area for gas flow through one or more first apertures from the compressed breathable gas source, second gas source, or both. The valve further includes a gear rotatable simultaneously in response to rotation of the first rotatable body and upon rotation of the gear adjusts a second cross-sectional area for flow through one or more second apertures of gas from the compressed breathable gas source, said second gas source, or both.

20 Claims, 19 Drawing Sheets

(56) References Cited

U.S. PATENT DOCUMENTS

| | | |
|---|---|---|
| 9,511,202 B1 | 12/2016 | Ratner |
| 2013/0199520 A1 | 8/2013 | Dhuper et al. |
| 2014/0069428 A1* | 3/2014 | Sears .................. F16K 11/0873 |
| | | 128/204.21 |
| 2016/0158477 A1 | 6/2016 | Dhuper et al. |
| 2019/0247599 A1 | 8/2019 | Lee et al. |

* cited by examiner

RESPIRATORY DEVICE

FIELD OF DISCLOSURE

The present disclosure relates in general to respirator valves designed for use within a respiratory device, and more specifically deals with flow generator devices.

BACKGROUND

Air flow generators use pressurized gas from gas sources to generate flow to a patient. Often, the air delivered to the patient is enriched with oxygen. A gas flow regulator may be used to regulate the oxygen intake flow rate and the oxygen concentration supplied to a patient by a breathing circuit. As stated, a flow generator may be connected to a pressured oxygen source as one gas source. One type of flow generator includes entrainment systems to provide a second air source. Often, entrainment air flow systems draw in atmospheric air to alter the oxygen concentration delivered to the patient by mixing the atmospheric air with the gas from the pressurized gas source using the venturi effect.

Venturi flow generators often have a valving system enabling various levels of atmospheric air to mix with the gas from a pressurized gas source. One drawback of current flow generators is the restriction of gas flow to the patient and imprecise oxygen concentrations delivered to the patient as a result of varying the oxygen flow rate.

Thus, there is a need for improvement in this field.

SUMMARY

The invention is defined by the claims and only the claims. As an example summary, this device and method may comprise a flow generator for use with a compressed breathable gas source. The flow generator includes a gas flow path adapted to deliver gas from the compressed breathable gas source to a patient delivery device. The flow generator further includes a gas connector operably attached to the compressed breathable gas source. The flow generator has a valve body operably located downstream of the gas connector and configured to selectively control a gas flow rate through the gas path downstream of the valve body. The valve body may be one variable aperture. In other embodiments, the valve body has at least two discrete apertures of varying size. In certain embodiments, the valve body has at least a first aperture, a second aperture and a third aperture or a solid surface. The flow generator may additionally include a nozzle operably located downstream of the valve body.

The valve body is selectively movable between at least first position placing the first aperture within the gas flow path, a second position placing the second aperture within the gas flow path and a third position placing the third aperture or the solid surface within the gas flow path. In the first position, the gas flow rate is a first flow rate. In the second position, the gas flow rate is a second flow rate lower than the first flow rate. In the third position, the gas flow rate is a third flow rate lower than the second flow rate.

The flow generator may further include an entrainment valve configured to selectively control the amount of atmospheric air entrained within the gas flow path. The atmosphere entrainment valve may be movable along a variable aperture. In other embodiments, the atmosphere entrainment valve is movable between at least two different positions. In yet other embodiments, the entrainment valve may be movable between more than two different positions, for example three. In each position different levels of atmospheric air are entrained into the gas flow path. The valve body and the entrainment valve may be controlled simultaneously by operating one of the valves.

Further disclosed is a valve for use with a compressed breathable gas source. The valve is adapted to: (a) be disposed upstream of a patient delivery device selected from the group comprising a mask, mouthpiece, nasal inlet, and combinations thereof, and (b) control at least a portion of a breathable gas source upstream of said patient delivery device and the source comprising both: (i) a compressed breathable gas source and (ii) a second gas source. In some embodiments, between a patient delivery device and control at least a portion of a breathable gas source means both gas sources that comprise the breathable gas source are on one side of the valve. In other embodiments, between a patient delivery device and control at least a portion of a breathable gas source means the valve may be disposed between the gas sources that comprise the breathable gas source.

The valve includes a first rotatable body. The first rotatable body adjusts, upon rotation thereof a cross-sectional area for gas flow through one or more first apertures from the compressed breathable gas source, second gas source, or both.

The valve may further include a gear rotatable simultaneously in response to rotation of the first rotatable body and upon rotation of the gear adjusts a second cross-sectional area for flow through one or more second apertures of gas from the compressed breathable gas source, the second gas source, or both. In some examples, during rotation the first cross-sectional area for gas flow may provide a consistent gas flow while the second cross-sectional area increases or decreases gas flow. In other examples, during rotation the first-cross sectional area for gas flow may increase or decrease gas flow while the second cross-sectional area for gas flow may provide a consistent gas flow.

DESCRIPTION OF THE SELECTED EMBODIMENTS

Figure 1:
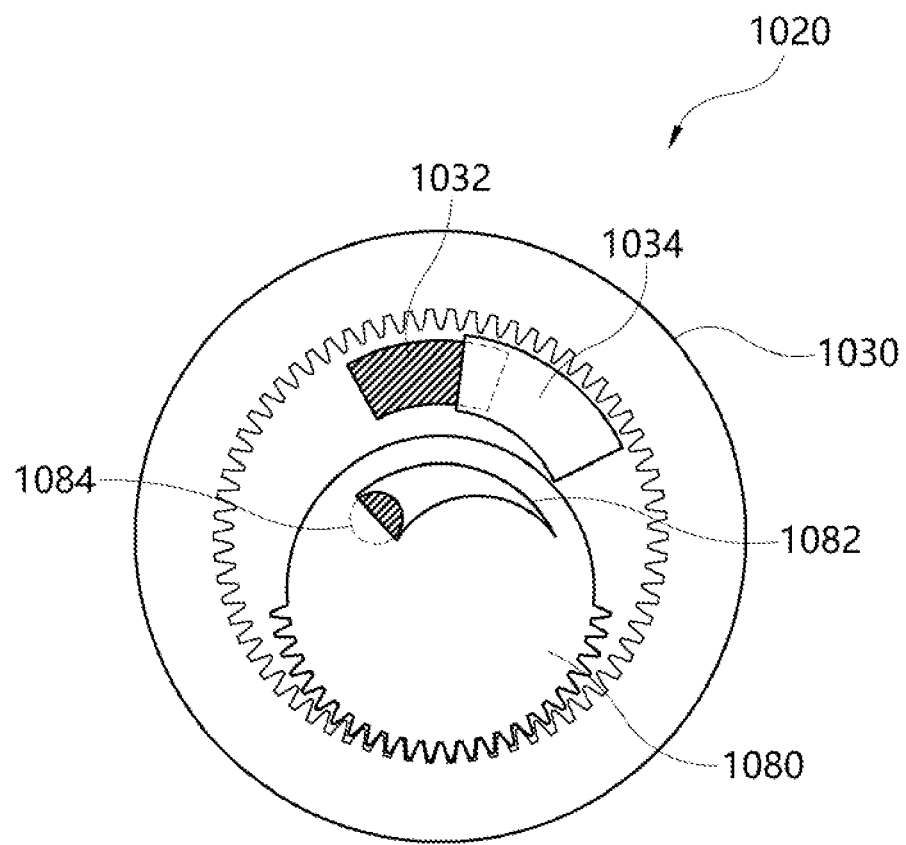
FIG. 1 is a schematic diagram view of a respirator valve.

For the purpose of promoting an understanding of the principles of the disclosure, reference will now be made to the embodiments illustrated in the drawings and specific language will be used to describe the same. It will nevertheless be understood that no limitation of the scope of the disclosure is thereby intended. Any alterations and further modifications in the described embodiments, and any further applications of the principles of the disclosure as described herein are contemplated as would normally occur to one skilled in the art to which the disclosure relates. Several embodiments of the disclosure are shown in great detail, although it will be apparent to those skilled in the relevant art that some features that are not relevant to the present disclosure may not be shown for the sake of clarity.

Figure 2:
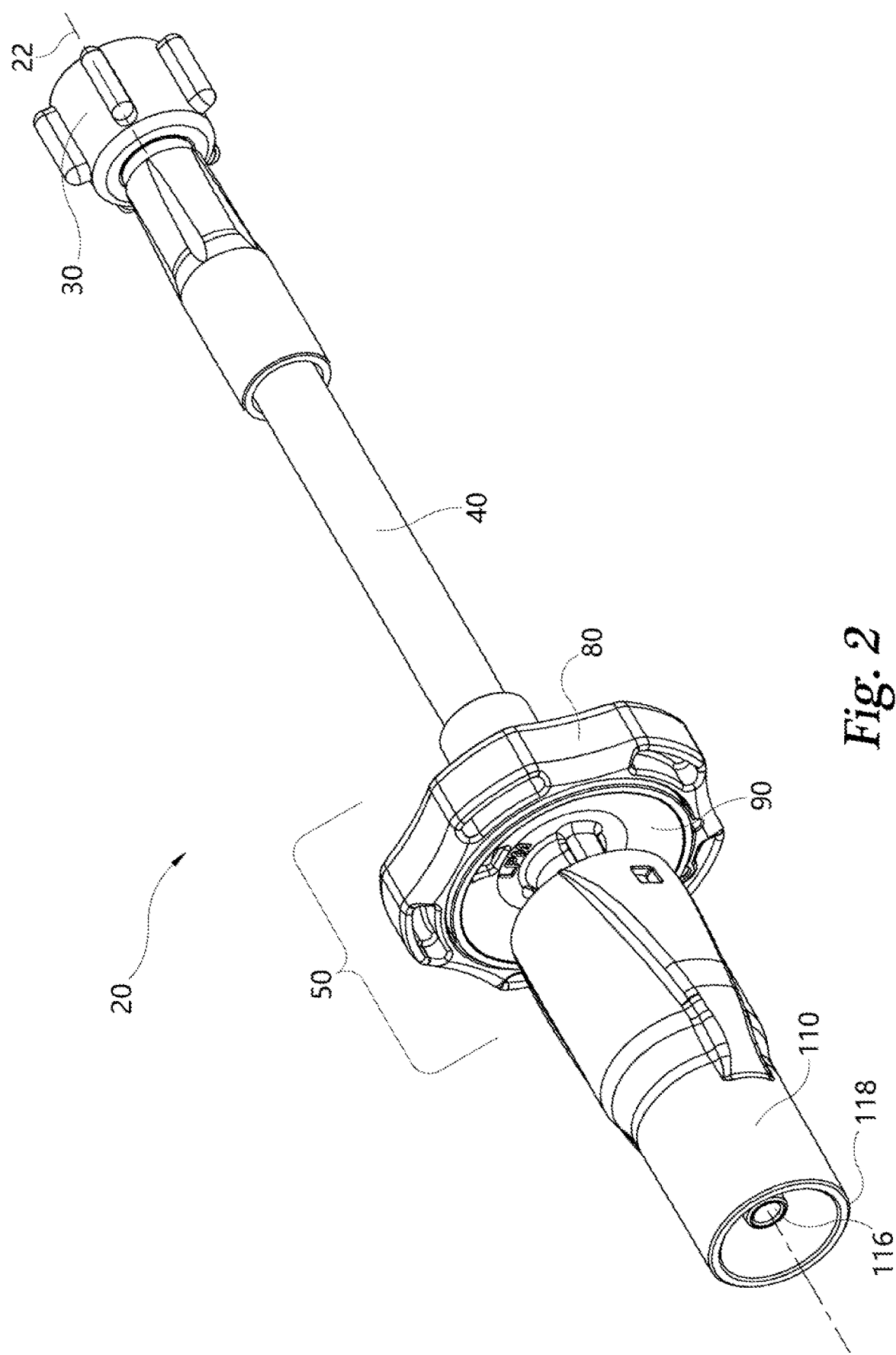
FIG. 2 is a perspective view of a flow generator or valve device.

As illustrated in FIG. 1, the present disclosure involves a respirator valve 1020 for use with a compressed breathable gas source (not illustrated). The valve 1020 may be adapted to be disposed upstream of a patient delivery device/breathable circuit (not illustrated) and control at least a portion of a breathable gas source upstream of the patient delivery device. The breathable gas source may include a first gas source and a second gas source. In some embodiments, between a patient delivery device and control at least a portion of a breathable gas source means both gas sources that comprise the breathable gas source are on one side of the valve. In other embodiments, between a patient delivery device and control at least a portion of a breathable gas source means the valve may be disposed between the gas sources that comprise the breathable gas source. The patient delivery device may be a mask, a mouthpiece, a nasal inlet or any combination thereof. The breathable gas source includes a compressed breathable gas source and a second gas source. FIG. 1 illustrated one example of continuously adjustable valving (optional) whereas FIG. 2 illustrates discrete valving (also optional).

The valve 1020 includes a first rotatable body 1030. When rotated, the first rotatable body 1030 adjusts a cross-sectional area for gas flow through one or more first aperture(s) 1032 from the compressed breathable gas source, second gas source or both. Some embodiments include at least two apertures, for example three apertures. The first rotatable body 1030 may include a cover 1034. Cover 1034 may be connected/integrated into rotatable body 1030. The first rotatable body may be rotated to fully uncover the aperture(s) 1032, partially block varying portions of the aperture(s) 1032 or completely block gas flow through the aperture(s) 1032.

The valve 1020 may further include a gear 1080 rotatable simultaneously in response to rotation of the first rotatable body 1030 or independently. The rotation of the gear 1080 adjusts a second cross-sectional area for flow through one or more second aperture(s) 1082 of gas from the compressed breathable gas source, the second gas source or both. The aperture may be tapered to allow decreasing levels of flow through the aperture when rotated or increasing levels of flow through the aperture when rotated in the opposite direction. Some embodiments include at least three apertures.

In other words, the gear 1080 may include an aperture(s) 1082 that when rotated aligns with a gas flow path 1084.

When the gear is rotated various levels of gas flow are allowed through aperture(s) 1082, depending on how aligned the aperture(s) 1082 are with the gas flow path 1084. In alternative embodiments, aperture(s) 1082 may vary in size. Therefore, one aperture may allow one gas flow rate while a second aperture allows a different gas flow rate.

In some embodiments, as the first rotatable body 1030 and gear 1080 are rotated simultaneously, the first rotatable body 1030 has a cover 1034 to block at least a portion of the aperture(s) 1032, preventing/decreasing gas flow through the aperture(s) 1032 from the compressed breathable gas source, second gas source or both. Concurrently, when the gear 1080 is rotated the aperture(s) 1082 allow a decreasing level of flow through the aperture(s) 1082. When rotated in the opposite direction, the rotatable body 1030 opens the aperture(s) 1032 to allow increasing levels of gas flow while the gear 1080 rotates allowing increasing levels of flow through the aperture(s) 1082.

In alternative embodiments, when rotated in one direction, the rotatable body 1030 may uncover/open at least a portion of the aperture(s) 1032, increasing gas flow. Concurrently, the gear 1080 decreases the level of flow through the aperture(s) 1082. When rotated in the opposite direction, the rotatable body 1030 closes the aperture(s) 1032 to allow decreasing levels of gas flow while the gear 1080 rotates allowing increasing levels of flow through the aperture(s) 1082. Any combination may be used to either increase or decrease gas flow through the aperture(s) 1032 associated with the rotatable body 1030 or the aperture(s) 1082 associated with the gear 1080 when rotated. Additionally, the rotatable body 1030 and gear 1080 can either rotate in the same direction simultaneously or if an additional gear or an odd number of gears are incorporated into the system, rotate in the opposite direction simultaneously. In some embodiments, the rotatable body 1030 and gear 1080 have the separate axes of rotation that extend parallel to each other.

In certain embodiment, during rotation, rotatable body 1030 may provide a continuous gas flow without increasing or decreasing the gas flow through aperture(s) 1032. Concurrently, gear 1080 may be rotated to increase or decrease the gas flow through aperture(s) 1082. In other words, rotation of rotatable body 1030 may provide the same gas flow through aperture(s) 1032 while gear 1080 rotates simultaneously increasing or decreasing gas flow through aperture(s) 1082.

In other embodiments, during rotation, rotatable body 1030 may provide an increasing or decreasing gas flow through aperture(s) 1032. Concurrently, during rotation, gear 1080 may provide a continuous gas flow without increasing or decreasing the gas flow through aperture(s) 1082. In other words, rotation of gear 1080 may provide the same gas flow through aperture(s) 1082 while rotation body 1030 rotates simultaneously increasing or decreasing gas flow through aperture(s) 1032.

The respirator valve 1020 may be used with any appropriate respirator/medical device, including CPAP machines, BiPAP machines, portable emergency oxygen systems, bag-valve-mask devices, home oxygen concentrators, nebulizers, etc. Additionally, the respirator valve 1020, as illustrated herein, may be used with a flow generator or more specifically a venturi flow generator.

FIG. 2-7 illustrate a flow generator and valve device 20. Device 20 defines a gas flow path from a gas connector/coupler 30 connected to a compressed breathable gas source (not illustrated) to a patient delivery device/breathable circuit (not illustrated). Gas flow path may include a longitudinal axis 22 extending along the entirety of the gas flow path. In additional embodiments, the longitudinal axis 22 may extend along a portion of the gas flow path. The gas connector 30 connects flow generator/device 20 to the compressed breathable gas source (not illustrated), such as a pressurized oxygen source. Gas connector 30 may be any of the well-known structures used to connect to a gas source.

In the illustrated embodiment, downstream of the gas connector 30 is a flexible member 40. Flexible member 40 may include a proximal end 42 and a distal end 44. Proximal end 42 is operably connected to gas connector 30 to allow gas from the compressed breathable gas source to pass through the portion of the gas flow path located within flexible member 40. Distal end 44 is connected to gas inlet valve assembly 50 at an upper inner gear housing 60. Flexible member 40 may be included in the system for ease of use, allowing some bend in the flexible member if the device 20 is bumped or the operator would like to move the device 20. It is understood that the flexible member 40 may be removed from the valve device 20. In embodiments without the flexible member 40, gas connector 30 may be directly couple to gas inlet valve assembly 50.

Figure 3:
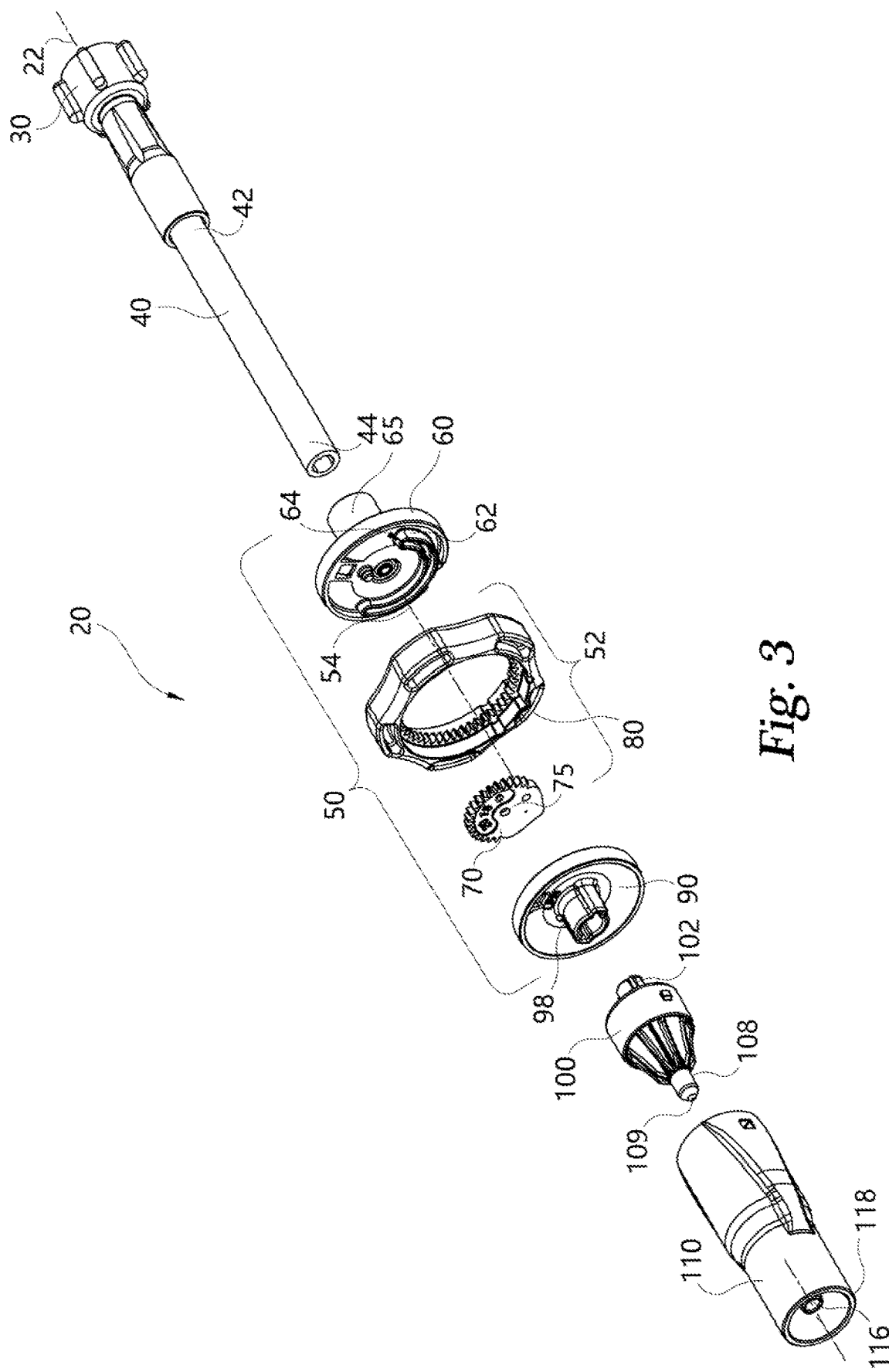
FIG. 3 is an exploded view of the device of FIG. 2.
Figure 4:
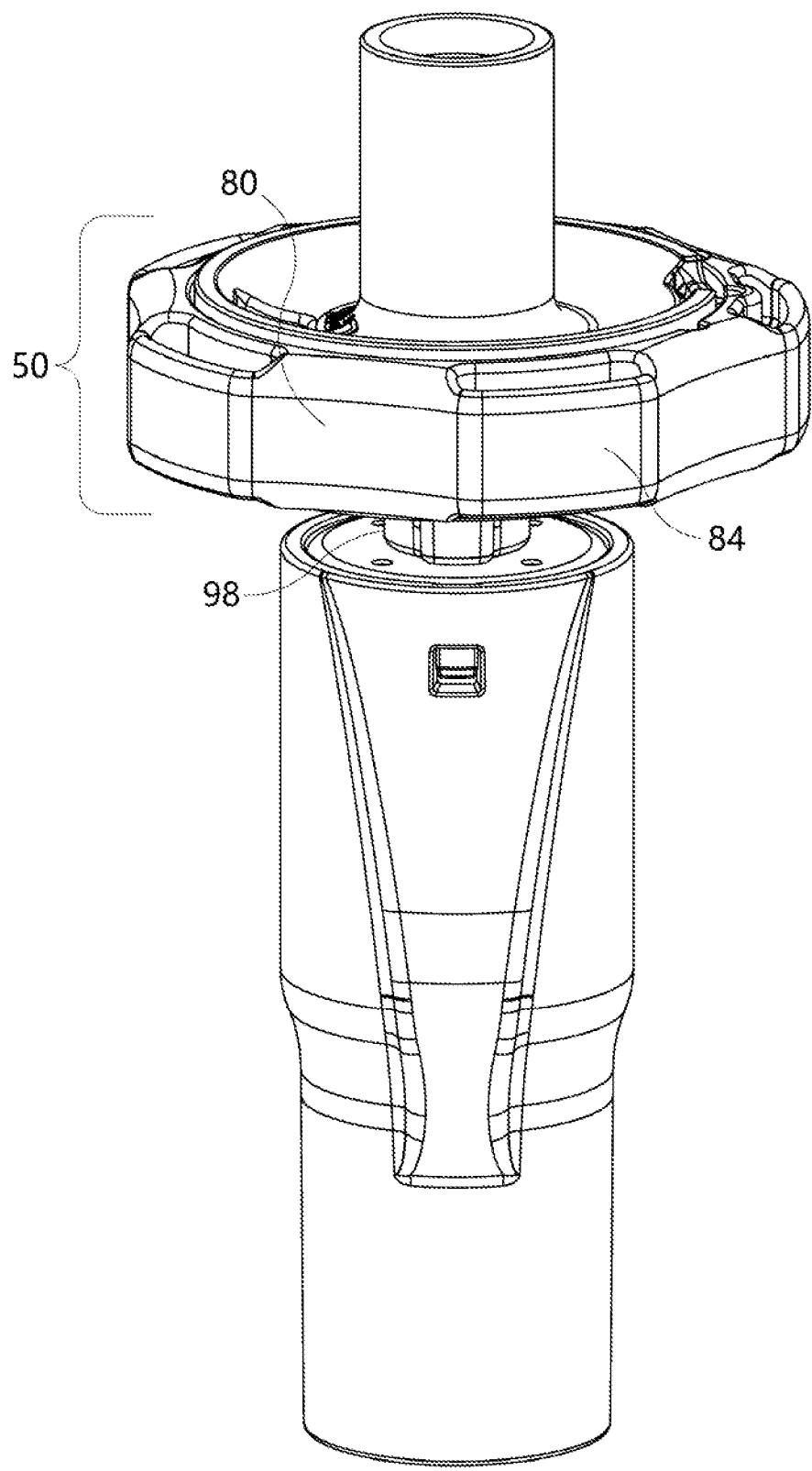
FIG. 4 is a perspective view of the device of FIG. 2 with a gas connector and a flexible member removed.
Figure 5:
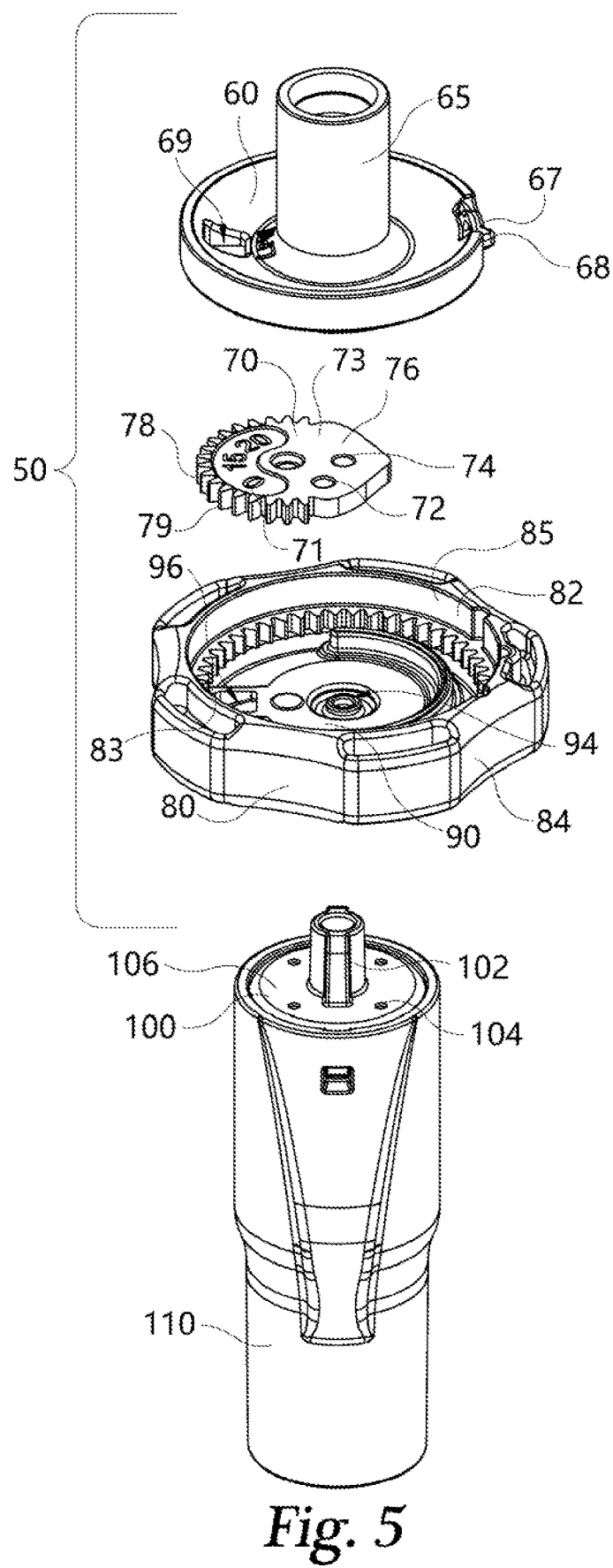
FIG. 5 is a partially exploded view of the device of FIG. 4.
Figure 6:
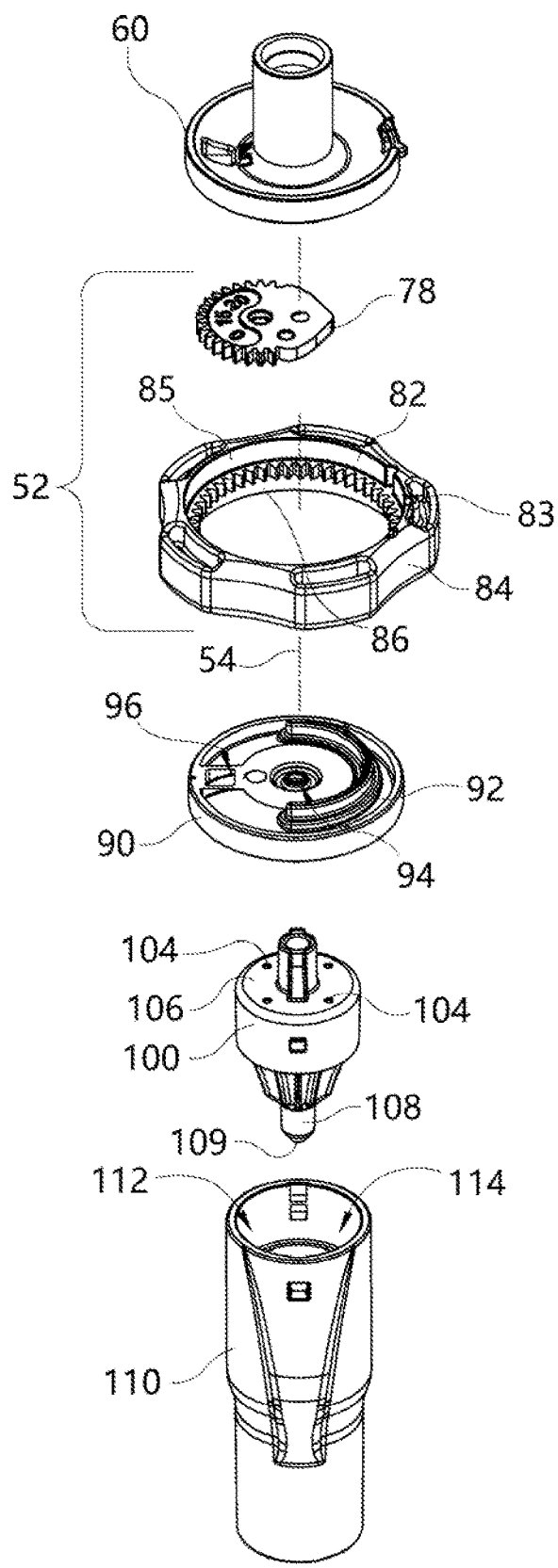
FIG. 6 is an exploded view of the device of FIG. 4.
Figure 7:
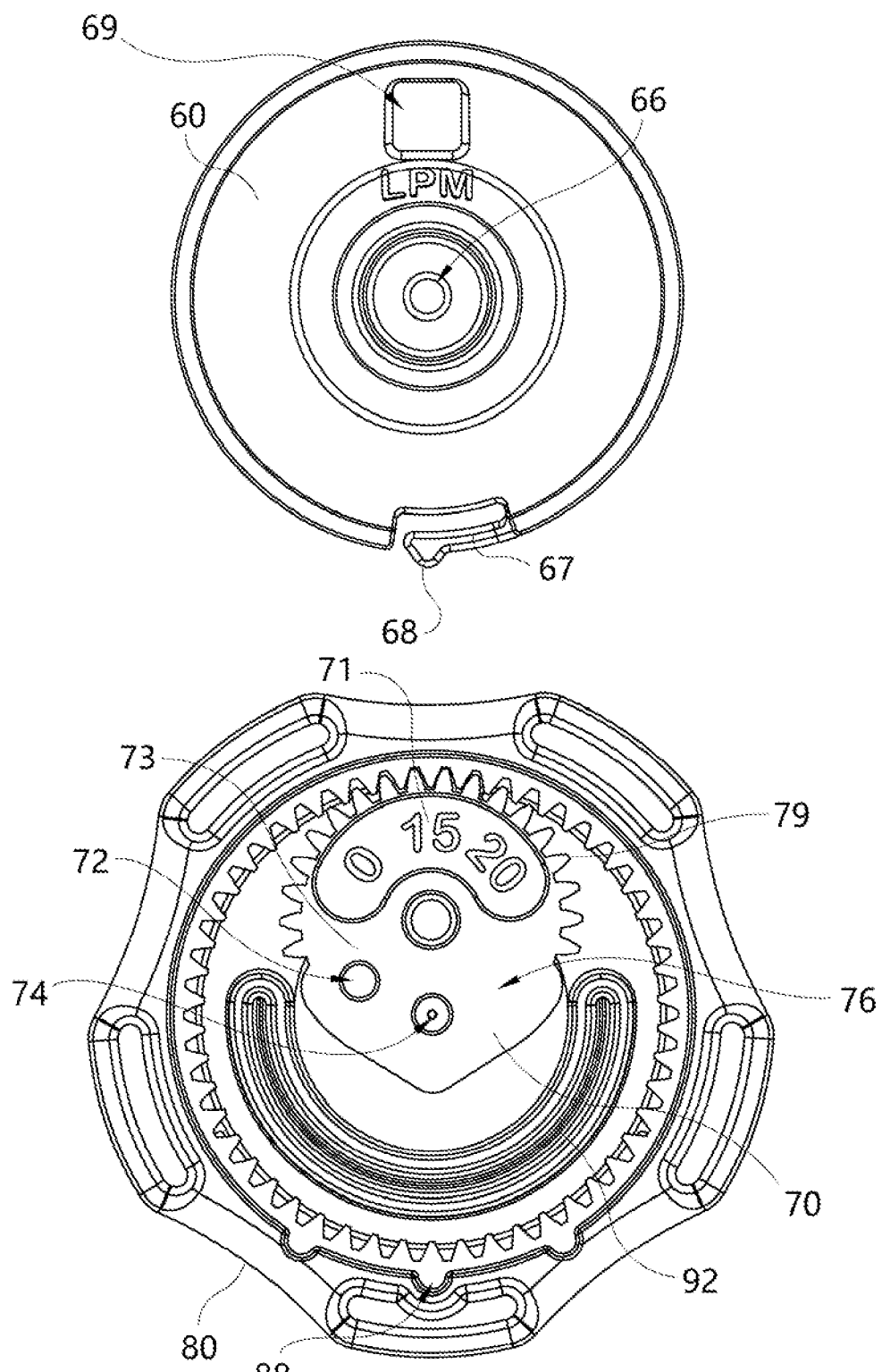
FIG. 7 is a top view of the device of FIG. 4 with an upper housing portion removed.
Figure 8:
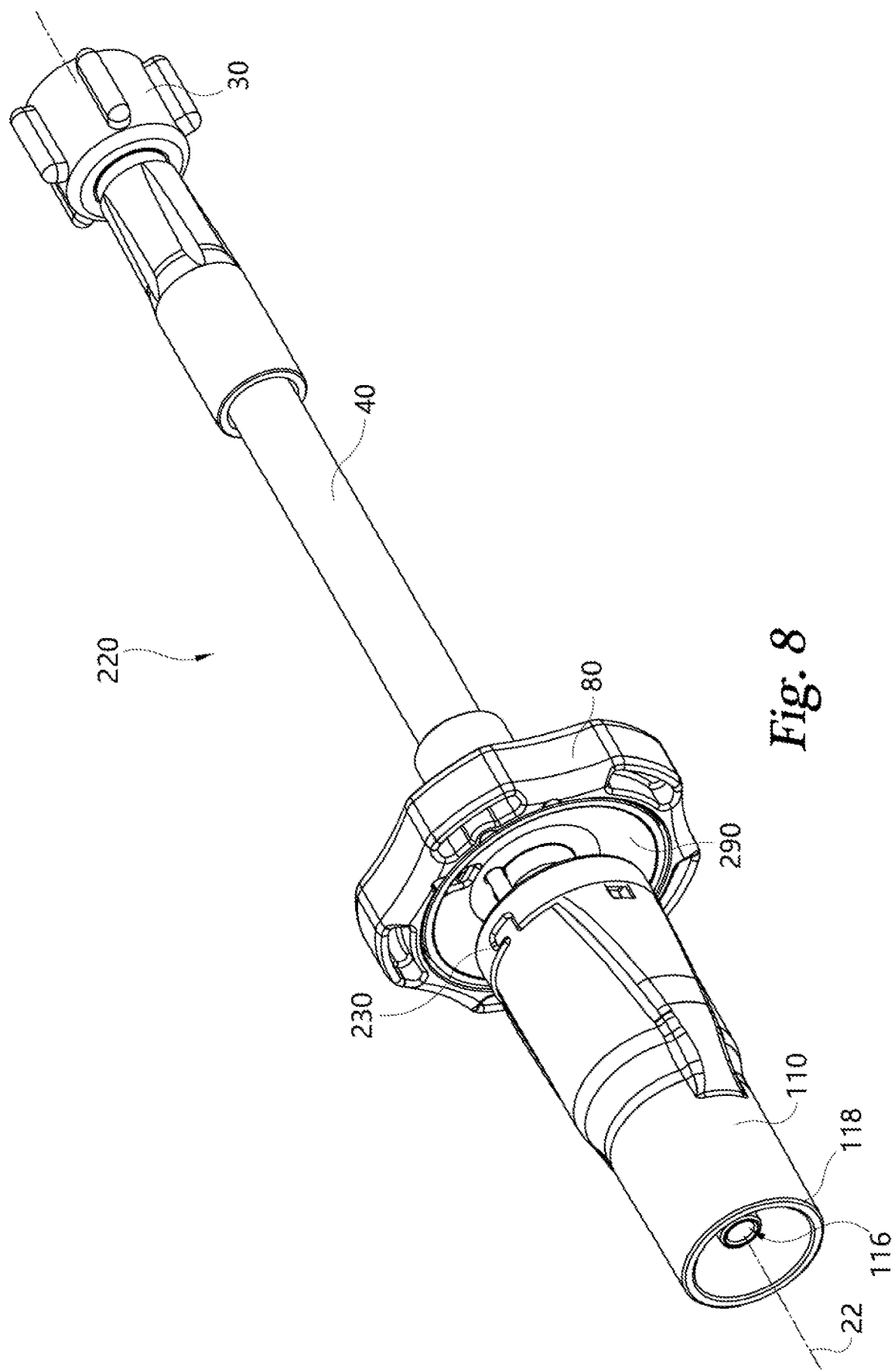
FIG. 8 is a perspective view of another embodiment of a flow generator or valve device.
Figure 9:
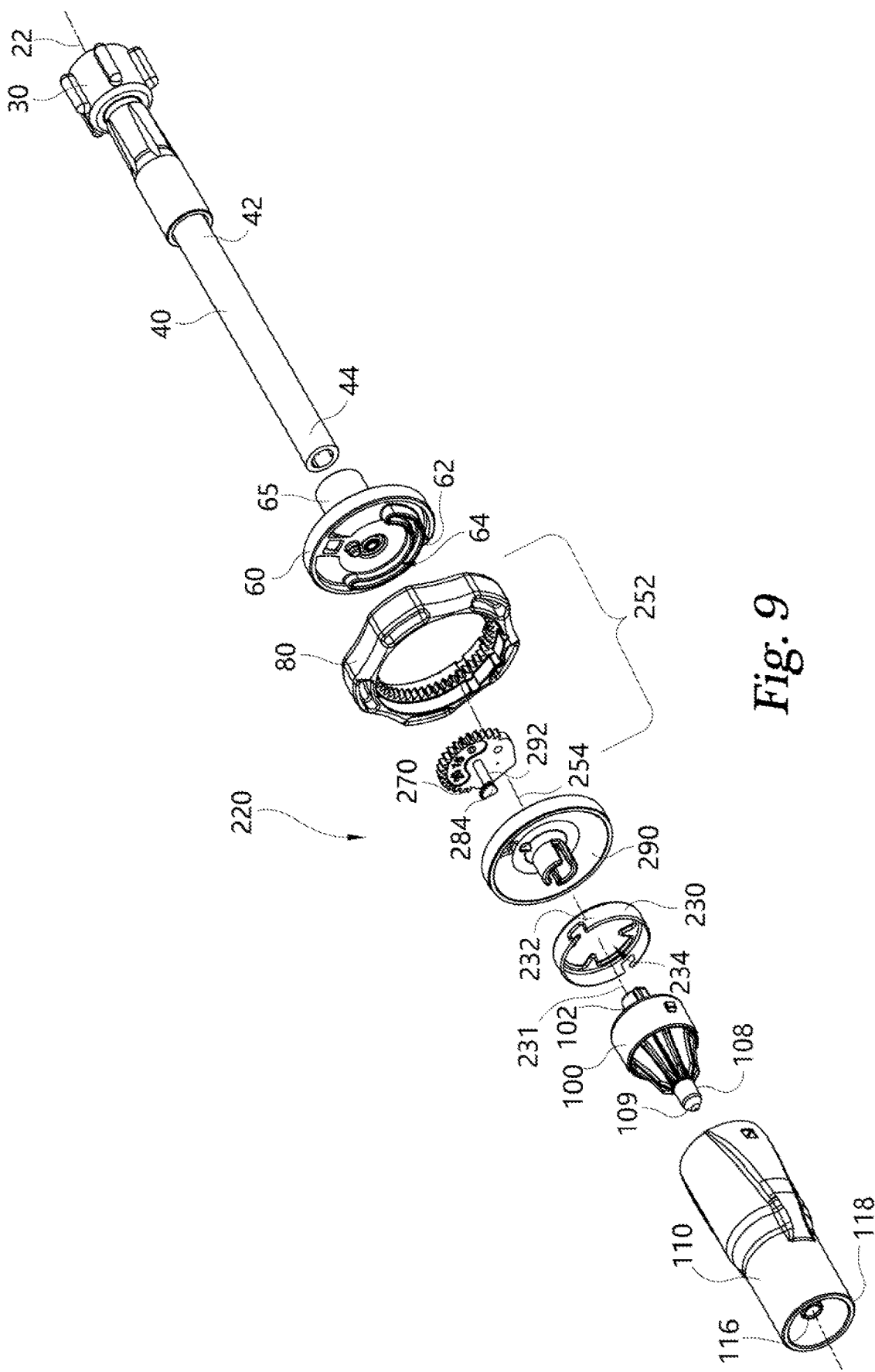
FIG. 9 is an exploded view of the device of FIG. 8.
Figure 10:
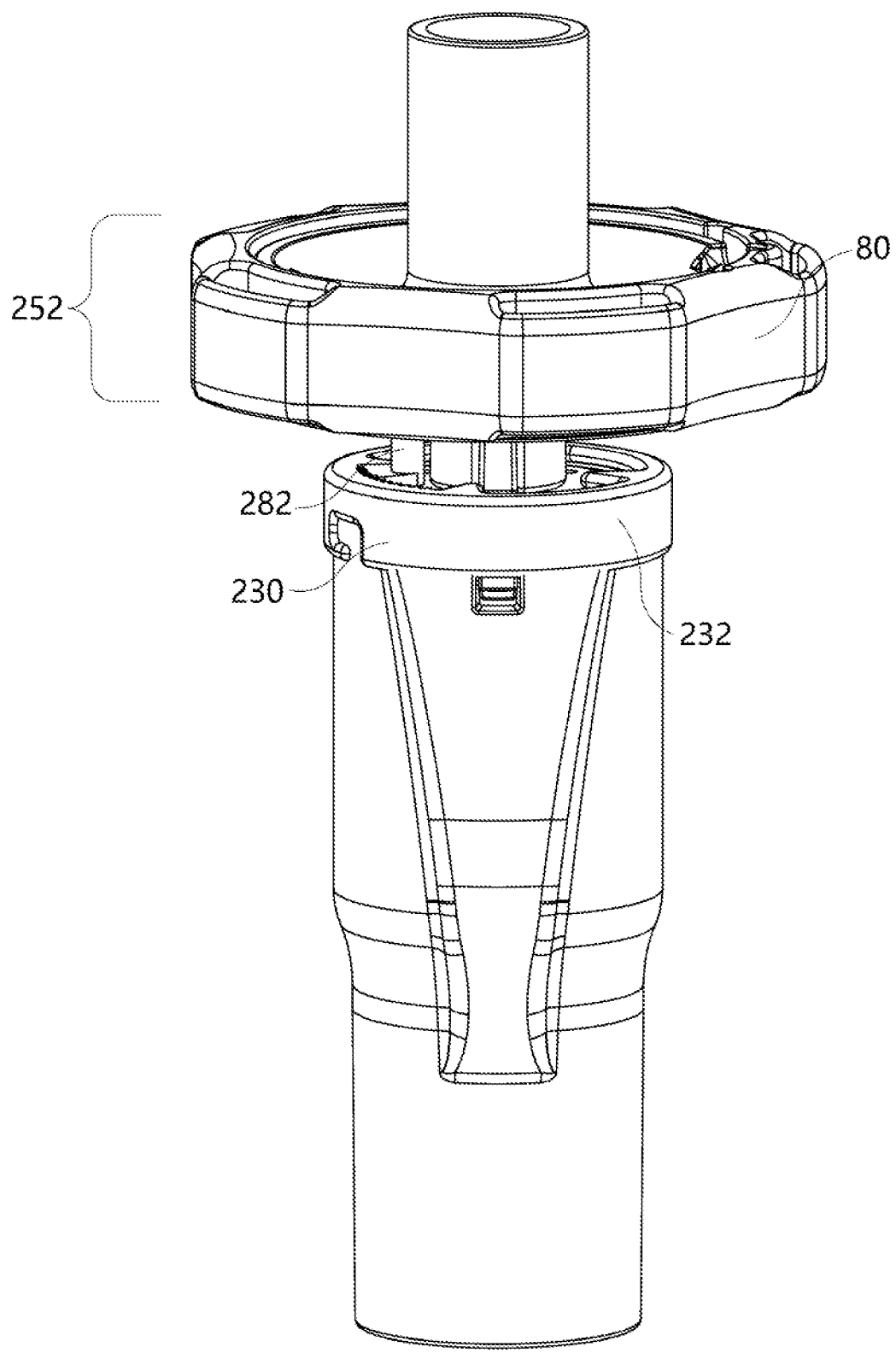
FIG. 10 is a perspective view of the device of FIG. 8 with a gas connector and a flexible member removed.
Figure 11:
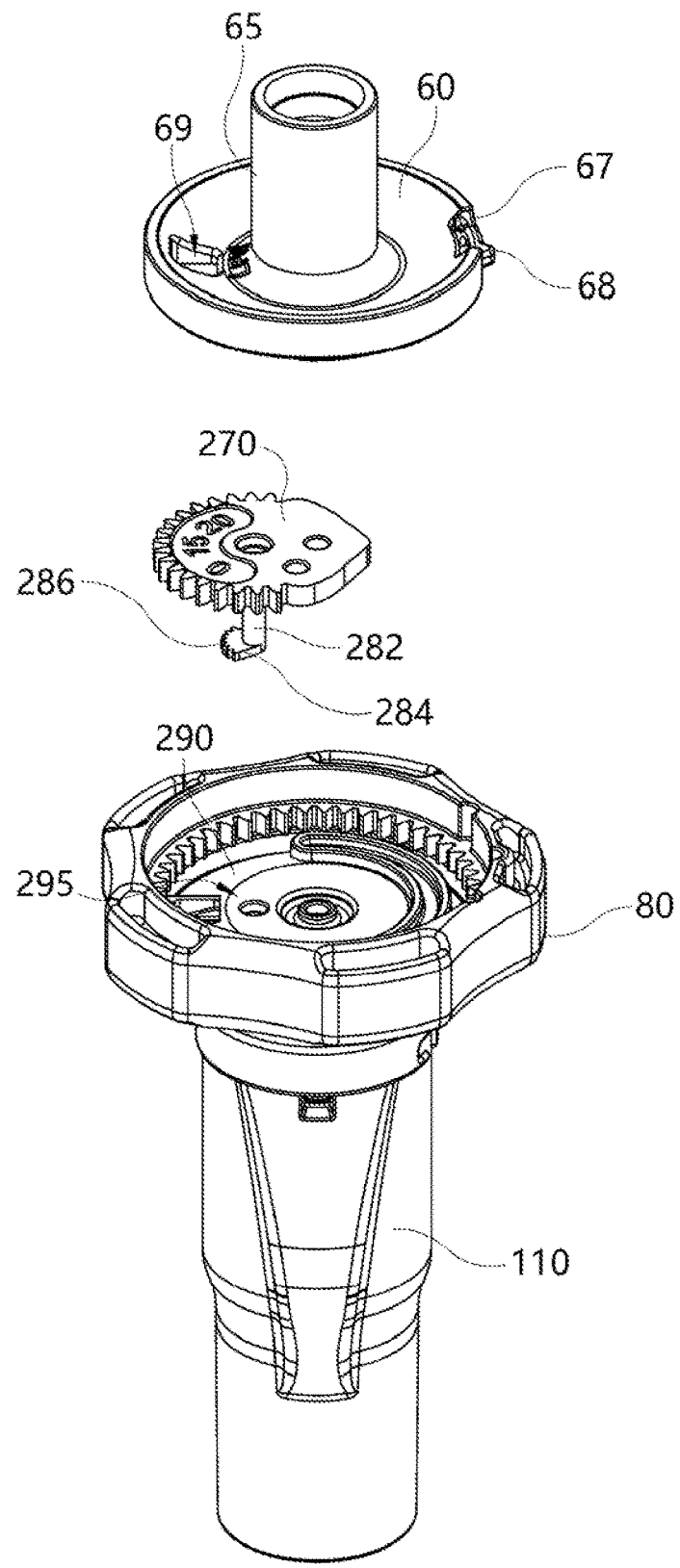
FIG. 11 is a partially exploded view of the device of FIG. 10.
Figure 12:
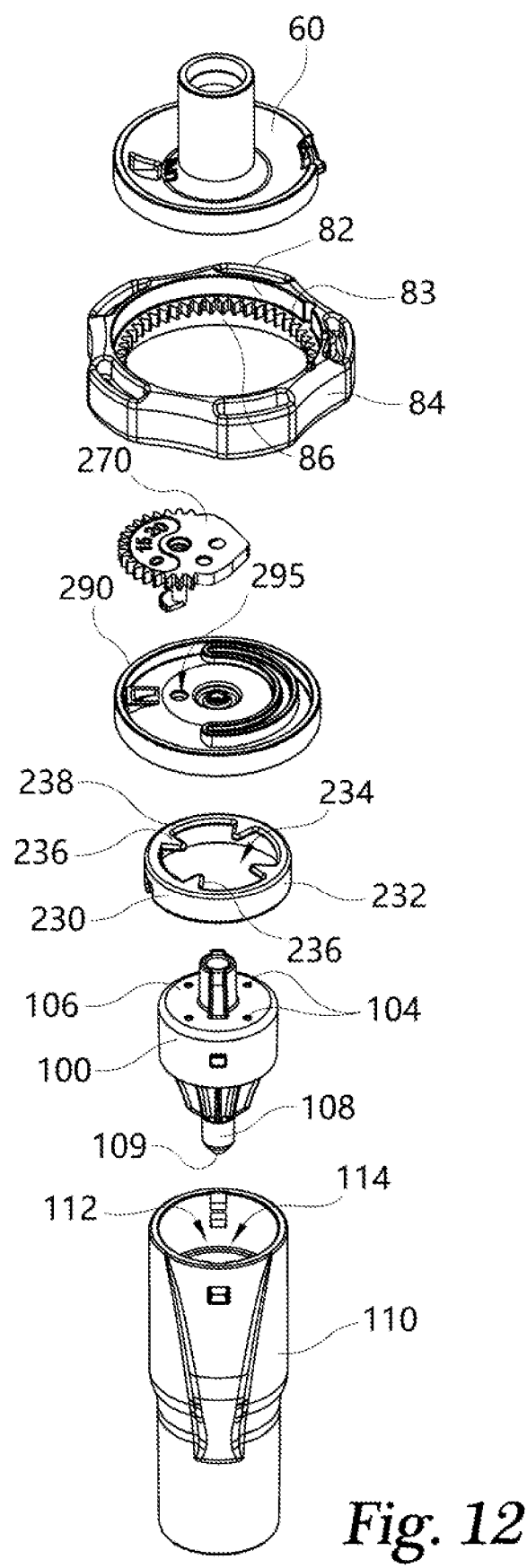
FIG. 12 is an exploded view of the device of FIG. 10.
Figure 13:
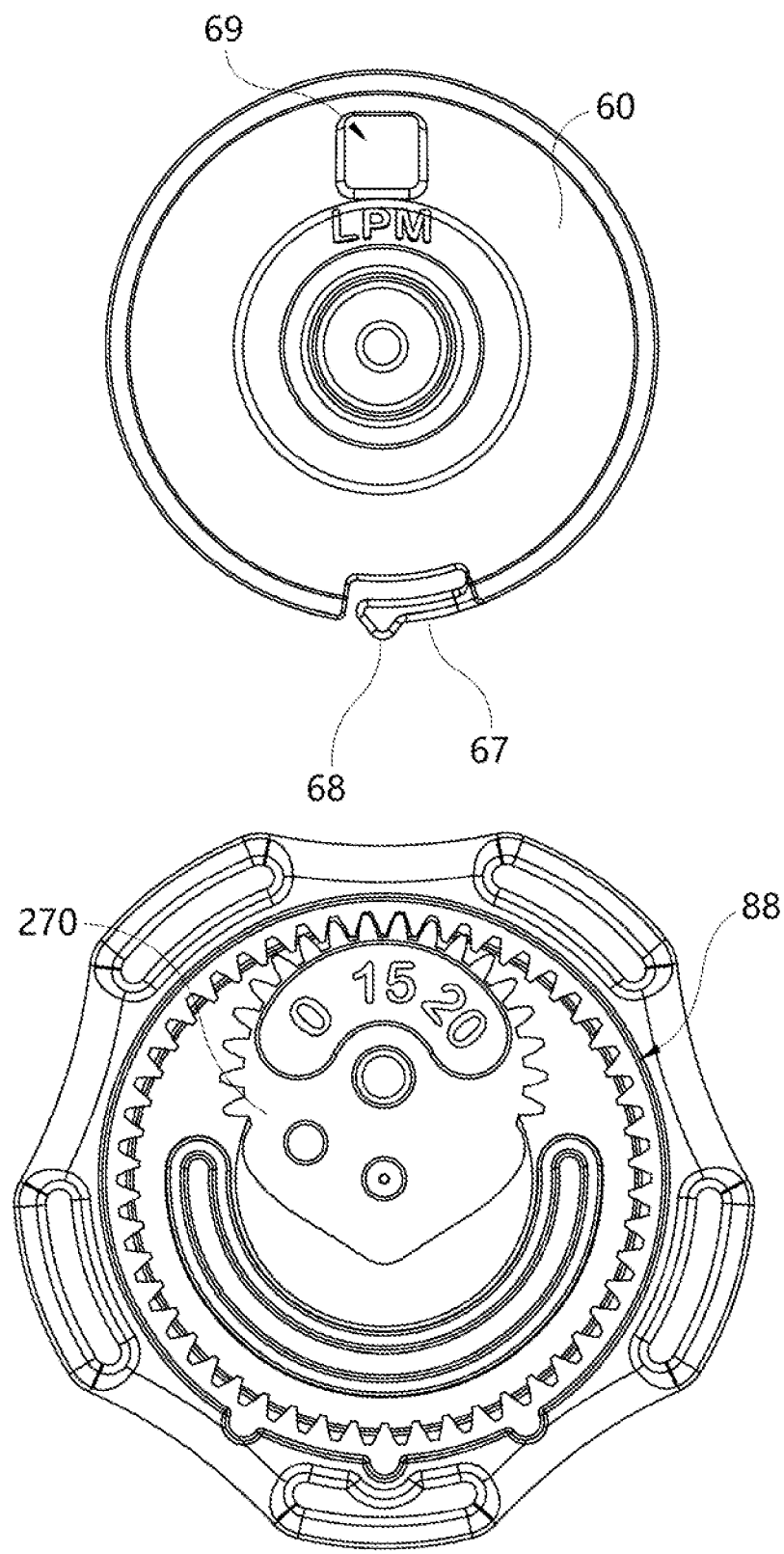
FIG. 13 is a top view of the device of FIG. 10 with an upper housing portion removed.
Figure 14:
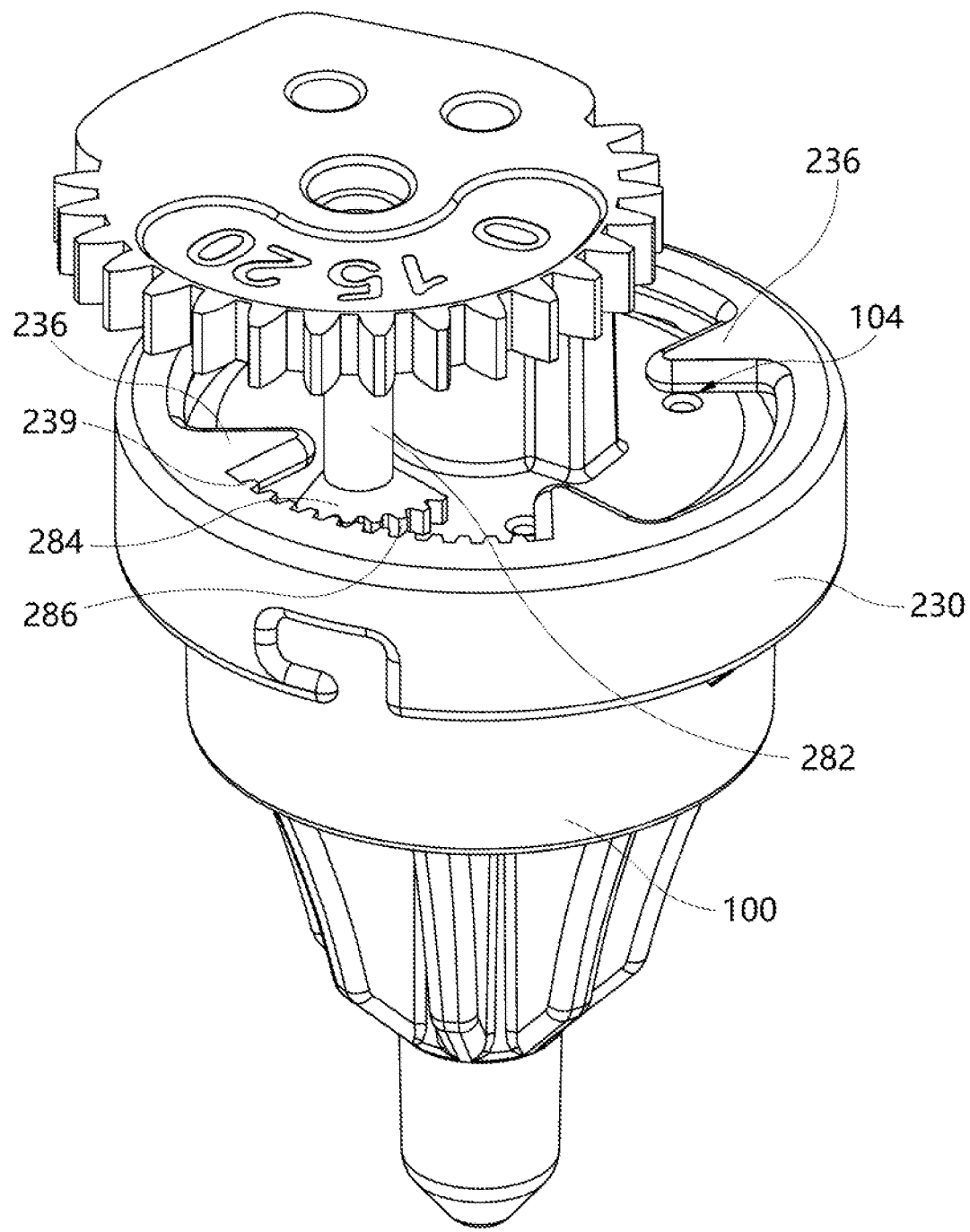
FIG. 14 is a perspective view of an inner gear engaging with an entrainment valve.
Figure 15:
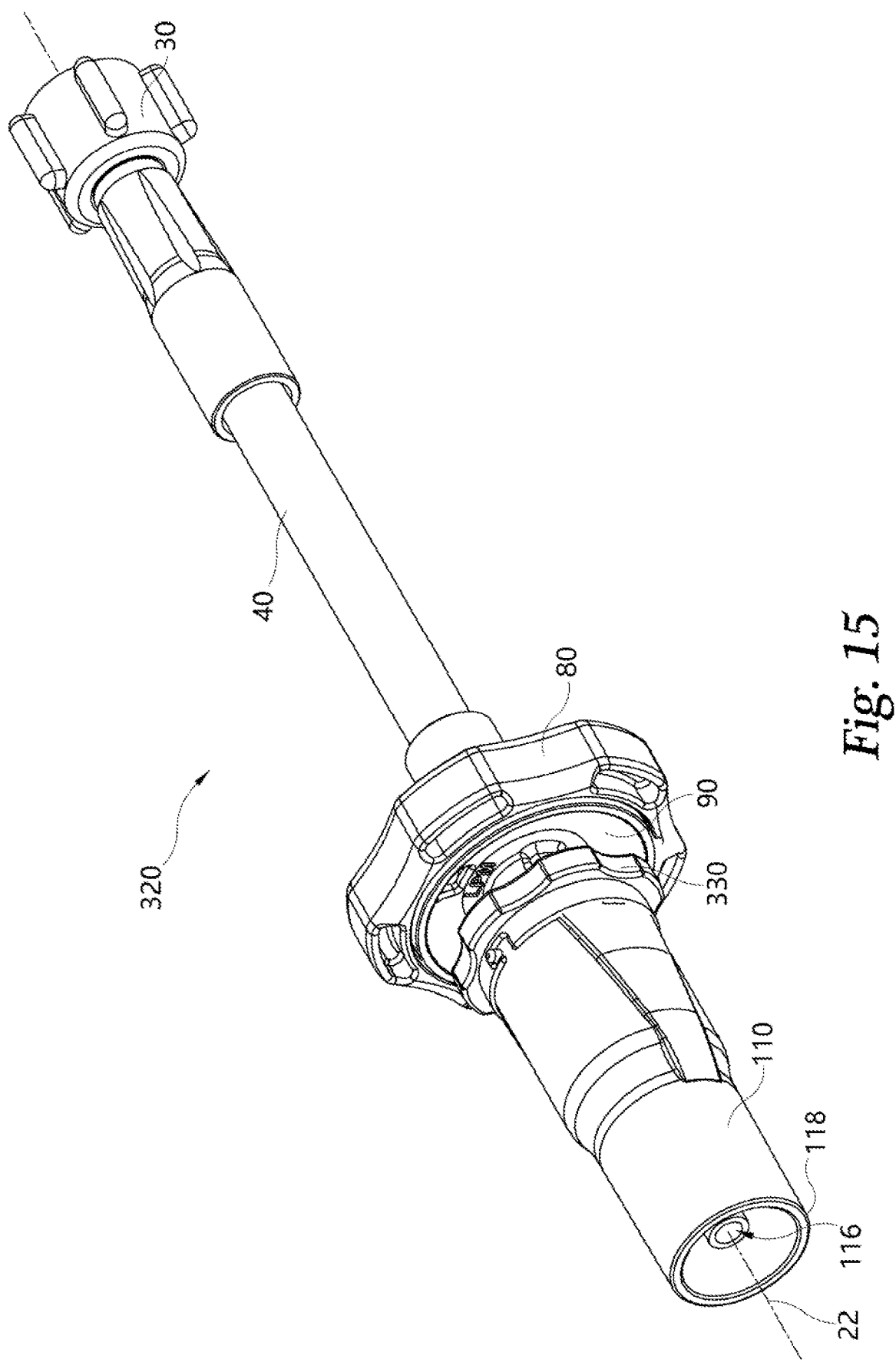
FIG. 15 is a perspective view of another embodiment of a valve.
Figure 16:
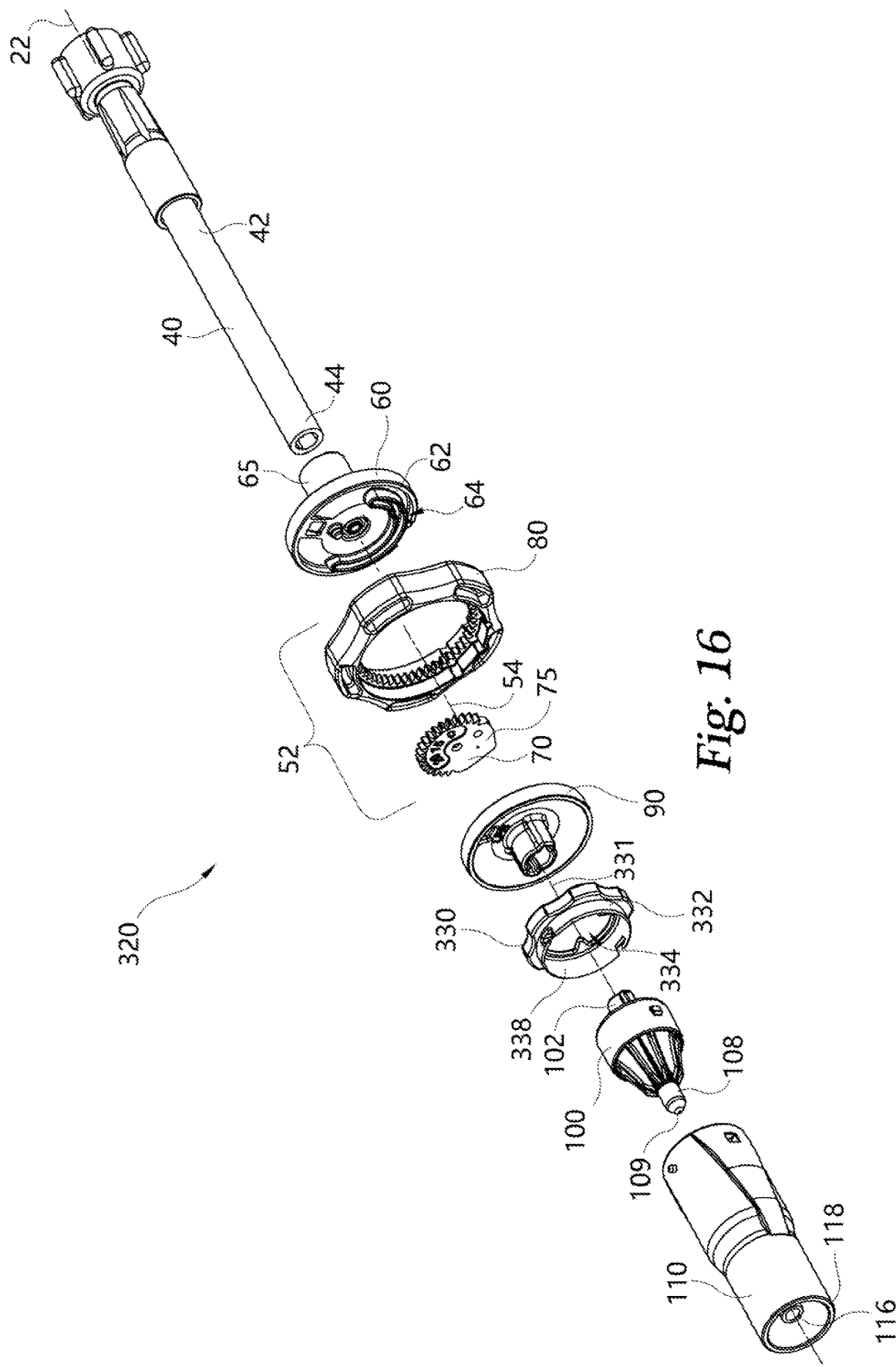
FIG. 16 is an exploded view of the device of FIG. 15.
Figure 17:
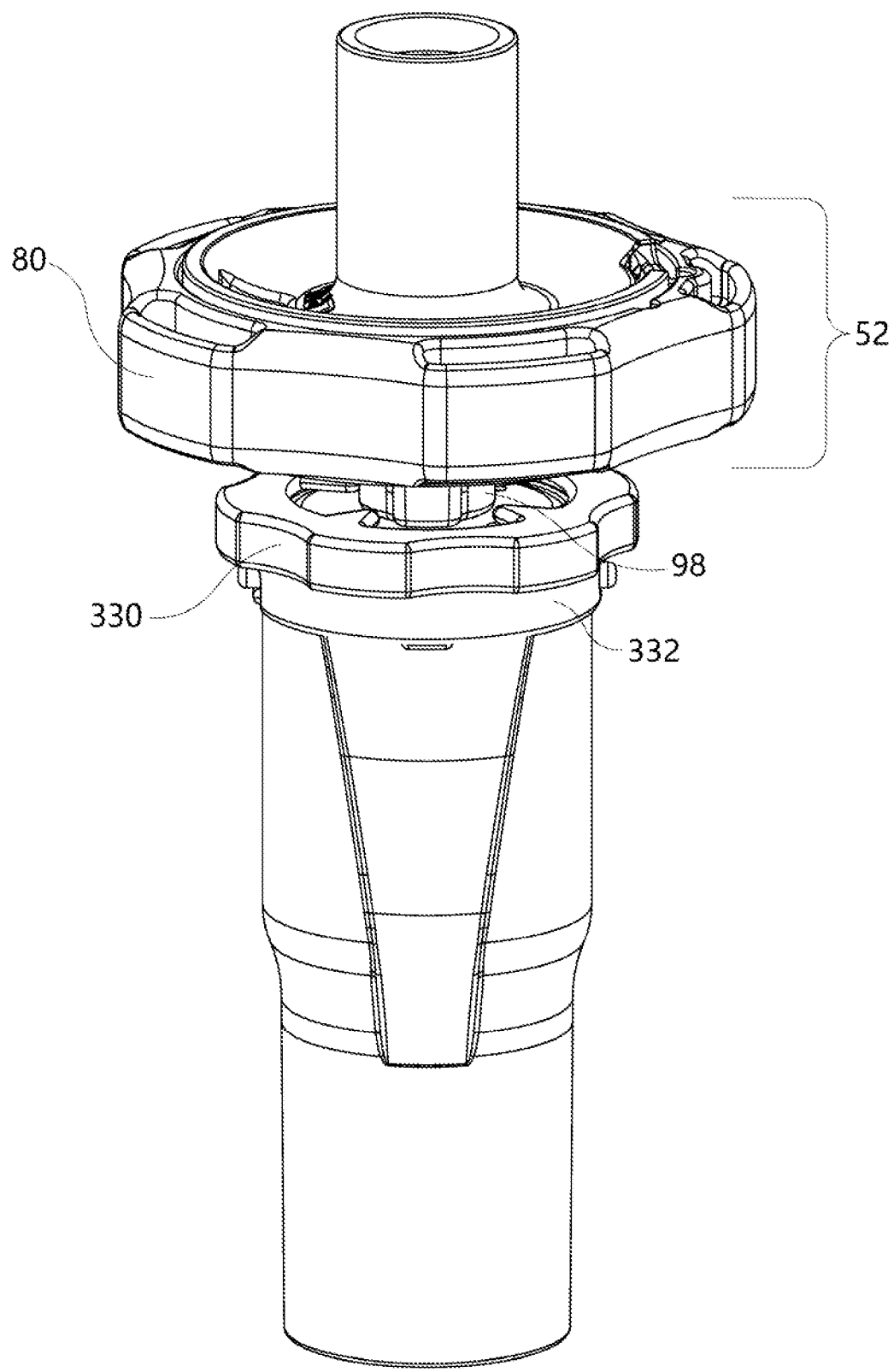
FIG. 17 is a perspective view of the device of FIG. 15 with a gas connector and a flexible member removed.
Figure 18:
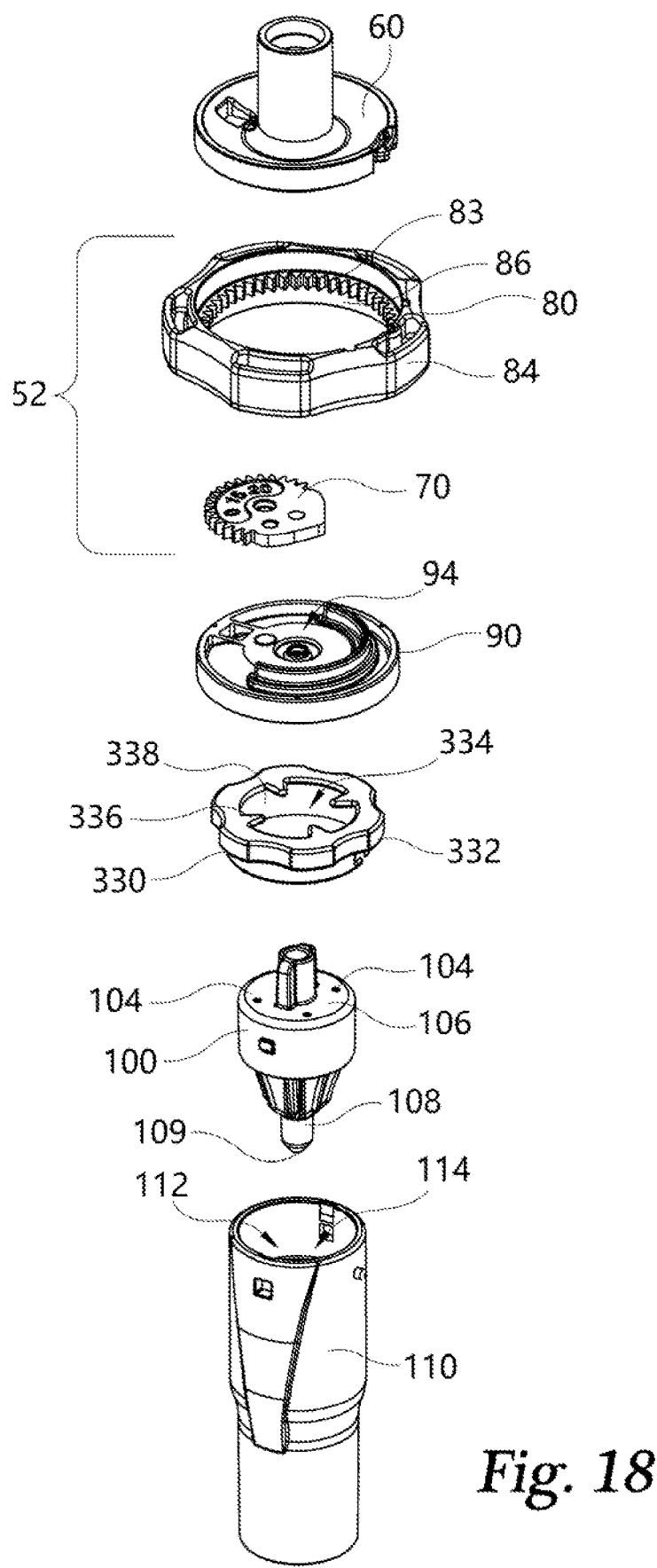
FIG. 18 is an exploded view of the device of FIG. 17.
Figure 19:
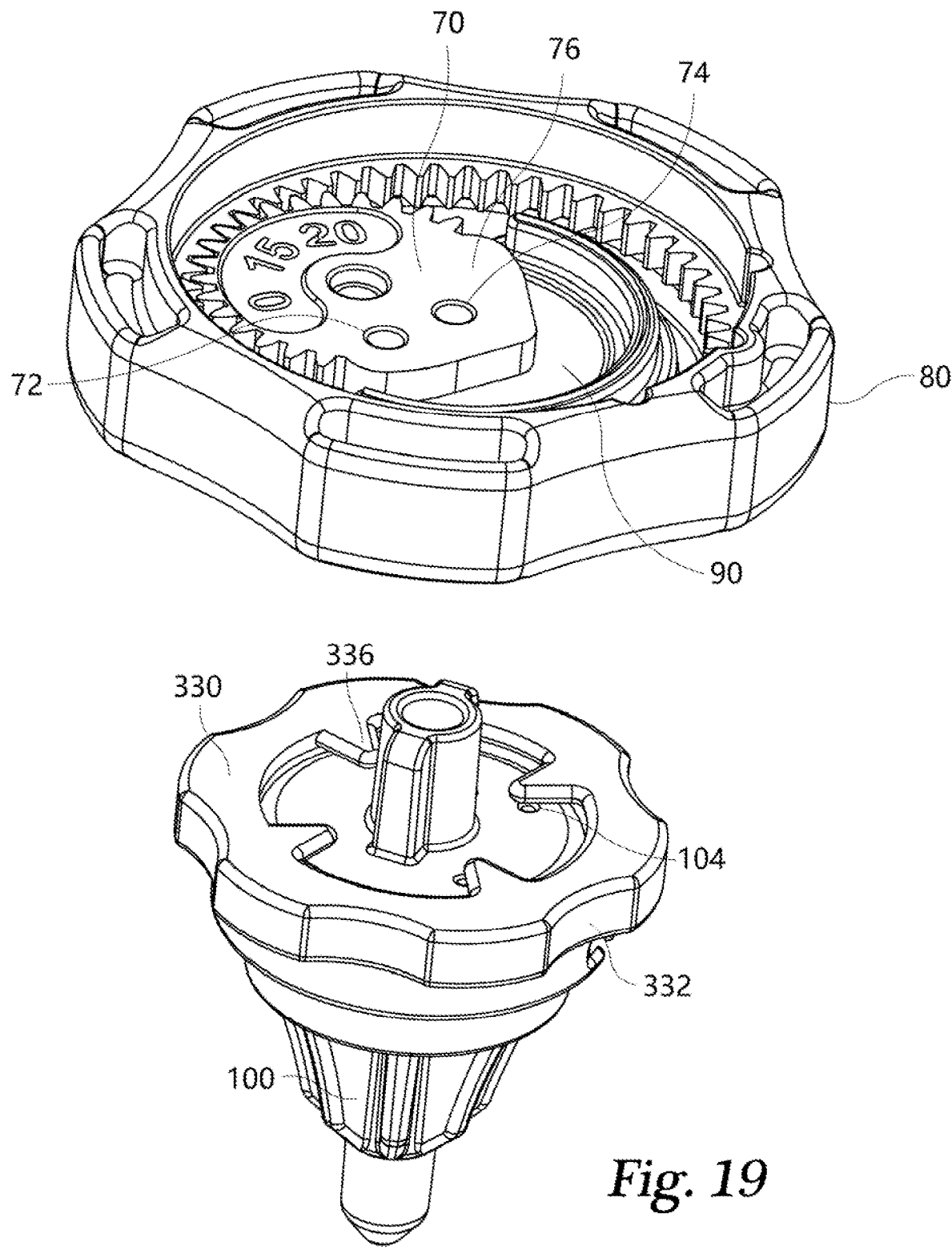
FIG. 19 is an exploded view of a valve body, an entrainment valve and a venturi body.

As seen in exploded FIG. 3, gas inlet valve assembly 50 includes a valve body 52. Valve body 52 is operably located downstream of the gas connector 30 and controls a gas flow rate through the gas flow path downstream of the valve body 52. Valve body 52 includes a longitudinal axis 54 that the valve body 52 is movable around. Longitudinal axis 54 extends parallel to the axis 22 of the gas flow path.

Valve body 52 may comprise at least two apertures, including a first aperture 72, a second aperture 74. In the illustrated embodiment, valve body 52 includes a third aperture or solid surface 76. The valve body 52 is movable between at least a first position, a second position and a third position. In the first position, the first aperture 72 is disposed within the gas flow path. In the second position, the second aperture 74 is disposed within the gas flow path. In the third position, the third aperture or solid surface 76 is disposed within the gas flow path. Each aperture may be a different size allowing differing amounts of gas to pass downstream of the valve body 52 to establish different gas flow rates downstream of the valve body 52. If in the third positon a solid surface is placed within the gas flow path, the gas flow rate is zero.

In one embodiment, the first aperture 72 may establish a first gas flow rate downstream of the valve body 52. The second aperture 74 may establish a second gas flow rate downstream of the valve body 52. In some examples, the second flow rate is lower than the first flow rate. The third aperture or solid surface 76 may establish a third gas flow rate downstream of the valve body 52. The third flow rate may be lower than the second flow rate. In some embodiments, the first gas flow rate is about 20 L/min. or a high flow rate, the second gas flow rate is about 15 L/min. or a low flow rate and the third gas flow rate is about 0 L/min or the gas intake is completely shut off. It is understood that the flow rates may be any appropriate flow rates within the therapeutic range. For example, the first flow rate may be 30 L/min., the second flow rate may be 20 L/min and the third flow rate may be 0 L/min. It is understood that any number of apertures establishing different flow rates may be defined through the valve body 50. It is further understood that the discussion of a first aperture, second aperture, etc. is only intended for illustrative purposes. The valve body may include apertures of varying size located in any desired order or configuration.

In the illustrated embodiment, valve body 52 is rotatable. Valve body 52 may be a rotary valve. The valve body includes a gearing system including an inner gear 70 engaging with an inner surface 82 of an outer ring gear 80. Ring gear 80 may at least partially encircle the inner gear 70. Inner gear may be an external gear and the ring gear may be an internal gear as defined below. In some embodiments, inner gear 70 defines the first aperture 72, the second aperture 74 and the third aperture or solid surface 76 extending through the inner gear. The inner gear 70 may be rotated into the first position aligning the first aperture 72 with the gas flow path, the second position aligning the second aperture 74 with the gas flow path or the third position aligning the third aperture or solid surface 76 with the gas flow path. Again, it is understood that inner gear 70 can define additional apertures and therefore be rotated into additional positions in order to align any number of apertures with the gas flow path. Inner gear 70 may further include indicators 71, such as numbers placed on an upper surface 73 and/or on a lower surface 75 of the inner gear 70, allowing the user to visualize the gas flow rate when rotating the inner gear 70. An outer surface 78 of the inner gear includes teeth 79.

Ring gear 80 may be a rotatable knob. Ring gear 80 may include an inner surface 82 and an outer surface 84. The inner surface 82 of ring gear may include a series of teeth 83. The series of teeth 83 may divide the inner surface 82 into an upper inner surface 85 and a lower inner surface 86. The series of teeth 83 may extend fully around the circumference of the inner surface 82. In some embodiments, the teeth 83 may extend partially around the circumference of the inner surface 82. The teeth 83 of the ring gear 80 may operably engage with the teeth 79 of the inner gear 70. This allows a user to simply rotate the ring gear 80 to correspondingly move the inner gear 70 between its various positions, placing the different apertures within the gas flow path to control gas intake flow.

Ring gear 80 may be circular to correspond with the overall shape of the inner gear 70. It is understood that ring gear 80 and inner gear 70 may be any appropriate shape to allow for the appropriate operational relationship between the two gears.

In alternative embodiments, the valve body 52 may be a slide valve. The valve body slides linearly, or along an arc, to move between the first position, the second position and the third position. In yet another embodiment, the valve body 52 may be a ball valve.

Gas inlet valve assembly 50 further includes an inner gear housing. The inner gear housing includes an upper housing portion 60 and a lower housing 90. When operably secured together, the inner gear 70 is disposed within the inner gear housing. Upper housing portion 60 and lower housing portion 90 include a connecting mechanism to secure the two portions together. Connecting mechanism may include a C-shaped flange 62 defining a trough 64 on one portion of the inner gear housing. The connecting mechanism may further include a protrusion 92 on the other portion of the inner gear housing. To secure the housing portions together, the protrusion 92 is received within the trough 64 defined by the flange 62. In the illustrated embodiment, the connecting method used is a C-shaped sonic weld join. Any other known mechanical or chemical bond connecting mechanism may be used, for example glues or snaps.

Upper housing portion 60 operationally receives distal end 44 of flexible member 40 within a receiving portion 65. Upper housing portion further includes an opening 66 located within the receiving portion 65 and extending through the upper housing portion 60 (see FIG. 6). Opening 66 defines a portion of the gas flow path upstream of the valve body 52. Upper housing portion 60 may be received and nested within the upper inner surface 85 of ring gear 80. Upper housing portion 60 includes a clip 67 with a tab 68 corresponding with a cavity 88 in the ring gear 80. Tab 68 is received by cavity 88 to lock the upper housing portion 60 with the ring gear 80. Upper housing portion 60 may further define a window 69. The window 69 allows the user to see the indicators 71 on the inner gear 70.

Lower portion 90 may be received and nested within the lower inner surface 86 of ring gear 80. Lower housing portion 90 may define an opening 94 downstream of the valve body 52 extending through the lower housing portion 90. Opening 94 defines a portion of the gas flow path passing downstream of the valve body 52. Lower housing 90 portion defines a window 96. The window 96 allows the user to see the indicators 71 on the inner gear 70. Lower portion 90 includes a structural member 98. Opening 94 may be disposed within the structural member 98. Structural member 98 may be a female portion for receiving a structural member 102 of a venturi body 100 with a male portion. It is understood that the male and female portions may be reversed.

Downstream of the gas inlet valve assembly 50 is body 100. Body 100 includes apertures 104 extending through a top 106 of the body 100. Apertures 104 may allow entrainment of atmosphere caused by the venturi effect created by the structure of the body 100. In the illustrated embodiment, body 100 includes four apertures 104. In alternative embodiments, body 100 may include any appropriate number of apertures.

Body 100 further includes a jet nozzle 108 operably located downstream of the valve body 52. Jet nozzle 108 includes a tapered gas outlet 109 at the top of its conical tip. During use, gas flow passes through the jet nozzle 108 and out its gas outlet 109. The gas passing out of gas outlet 109 is low pressure, causing atmospheric air to entrain into the gas flow path resulting in a change to the oxygen concentration within the gas flow path.

Body 100 may be at least partially nested within a venturi housing 110. Venturi housing 110 may define a hollow interior 112 to receive the venturi body 100. The hollow interior 112 may further define a mixing chamber 114. Within the mixing chamber 114, gas from the compressed breathable gas source and atmospheric air may be mixed to a predetermined oxygen concentration. Venturi housing 110 includes an outlet 116 allowing gas to pass out of the mixing chamber 114 and out of the venturi housing 110. Venturi housing 110 further includes structural member 118 for connecting the patient delivery device. In alternative embodiments the patient delivery device can be directly connected to the outlet 116.

Optionally, the first and second valve bodies may be inverted so they control the opposite flow paths (e.g. first vs. second) from the examples disclosed. Thus, for example, when compressed breathable gas is used its flow may be controlled (discretely or continuously) by the other valve body as shown in the drawing examples. Likewise, optionally the valving structure may remain as illustrated, but the first and second flow paths inverted. Either optional variation may still provide simultaneous valving of the two flows.

Representatively illustrated in FIGS. 8-14 is another embodiment of a valve device, also with a flow generator/device 220. Flow generator/device 220 allows a user to control the gas flow rate from the compressed breathable gas source and the oxygen concentration within the gas flow path simultaneously. Flow generator/device 220 is comparable to flow generator/device 20. The applicable discussion above is incorporated herein. For the sake of brevity, only the differences between flow generator/device 220 and flow generator/device 20 are discussed below in reference to flow generator/device 220.

Device 220 may further include an entrainment valve 230 configured to selectively control the amount of atmosphere entrained into the gas flow path. Entrainment valve 230 is mounted flush over the top 106 of body 100. Entrainment valve 230 may be rotatable. Entrainment valve 230 may include a circular body 232 defining an opening 234 through the center of the valve 230. Entrainment valve 230 may include a series of protrusions 236 extending inwardly from an inner surface 238 of the circular body 232. When the entrainment valve 230 is rotated, protrusions 236 cover various portions of apertures 104 on body 100. Entrainment valve 230 may be rotated to fully expose apertures 104 to the atmosphere allowing the highest level of atmosphere to be entrained within the gas flow path, a portion of the aperture 104 to allow a lower level of atmosphere to be entrained within the gas flow path or completely close the aperture 104 so that no atmosphere may be entrained within the gas flow path. Entrainment valve 230 may include a longitudinal axis 231 parallel to axis 254 of the valve body 252 and axis 22 of the gas flow path. In some embodiments, axis 231 and axis 254 are the same axis. When axis 231, axis 254 and axis 22 are the same axis, entrainment valve 230 and valve body 252 have the same axis of rotation.

Inner gear 270 of valve body 252 may include a connecting member with a shaft 282 and a protrusion 284 with a series of teeth 286. The connecting member extends through a second opening 295 in the lower housing portion 290 and engages with the entrainment valve 230. When the inner gear 270 is rotated, the connecting member is rotated around the same plane. Entrainment valve 230 further includes a series of teeth 239 along a portion of the inner surface 238 of the circular body 232. The teeth 239 of entrainment valve 230 engage the teeth 286 of connecting member so that when the inner gear 270 is rotated, the entrainment valve 230 is rotated simultaneously. Advantageously, this allows the user to adjust the oxygen concentration and gas flow rate within the gas flow path simultaneously.

The flow generator or device 220 may have a predetermined gas flow rate and corresponding oxygen concentration. For example, when the valve body 252 is rotated to allow a gas flow rate of 15 L/min, the entrainment valve 230 would rotate simultaneously to allow the entrainment of atmosphere to establish an 80% oxygen concentration within the gas flow path. If the valve body 252 is rotated to allow a gas flow rate of 20 L/min, the entrainment valve 230 would rotate to establish a 70% oxygen concentration. In an alternative embodiment, the inner gear 270 of the valve body 252 may include multiple apertures at the same gas flow rate. For example, when valve body 252 is rotated to allow a gas flow rate of 15 L/min, the entrainment valve 230 would rotate simultaneously to allow the entrainment of atmosphere to establish an 80% oxygen concentration within the gas flow path. If the valve body 252 is rotated again, it may still allow a gas flow rate of 15 L/min, but at a 60% oxygen concentration due to the rotation of the entrainment valve 230. It is understood that these are non-limiting examples and the device may be configured to allow any combination of gas flow rates and oxygen concentrations within the gas flow path.

Representatively illustrated in FIGS. 15-19 is another embodiment of a device 320. Device 320 allows a user to control the gas flow rate from the compressed breathable gas source and the oxygen concentration within the gas flow path independently. Device 320 is comparable to the devices or valves 20, 220 disclosed above. The applicable discussion above is incorporated herein. For the sake of brevity, the differences are discussed below in reference to device 320.

Device 320 includes the valve body 52 as described in FIGS. 2-7. Device 320 may further include an entrainment valve 330 configured to selectively control the amount of atmosphere entrained into the gas flow path. As illustrated, entrainment valve 330 may be mounted flush over the top 106 of body 100. Entrainment valve 330 may be a rotatable knob. Entrainment valve 330 may include a substantially circular body 332 defining an opening 334 through the center of the valve 330. Entrainment valve 330 may include a series of protrusions 336 extending inwardly from an inner surface 338 of the circular body 332. When the entrainment valve 330 is rotated, protrusions 336 cover various portions of apertures 104 on body 100. Entrainment valve 330 may be rotated to fully expose apertures 104 to the atmosphere allowing the highest level of atmosphere to be entrained within the gas flow path, a portion of the aperture 104 to the atmosphere or completely close the aperture 104 so that no atmosphere may be entrained within the gas flow path. Entrainment valve 330 may include a longitudinal axis 331 parallel to the axis 54 of the valve body 52 and the axis 22 of the gas flow path. In some embodiments, axis 331, axis 54 and axis 22 are the same axis. When axis 331 and axis 52 are the same axis, entrainment valve 330 and valve body 52 have the same axis of rotation.

The valve body openings may be discreet (see FIG. 19) or continuous (as shown in FIG. 1) or a combination thereof.

Entrainment valve is independently movable in relation to the valve body. For example, the valve body may be rotated to allow a gas flow rate of 15 L/min, independently the oxygen concentration within the gas flow path may be adjusted by rotating the entrainment valve to allow a desired amount of atmosphere to entrain into the gas flow path.

Glossary of Terms

While examples of the disclosure are illustrated in the drawings and described herein, this disclosure is to be considered as illustrative and not restrictive in character. The present disclosure is exemplary in nature and all changes, equivalents, and modifications that come within the spirit of the disclosure are included. The detailed description is included herein to discuss aspects of the examples illustrated in the drawings for the purpose of promoting an understanding of the principles of the disclosure. No limitation of the scope of the disclosure is thereby intended. Any alterations and further modifications in the described examples, and any further applications of the principles described herein are contemplated as would normally occur to one skilled in the art to which the disclosure relate. Some examples are disclosed in detail, however some features that may not be relevant may have been left out for the sake of clarity.

Where there are references to publications, patents, and patent applications cited herein, they are understood to be incorporated by reference as if each individual publication, patent, or patent application were specifically and individually indicated to be incorporated by reference and set forth in its entirety herein.

Singular forms "a", "an", "the", and the like include plural referents unless expressly discussed otherwise. As an illustration, references to "a device" or "the device" include one or more of such devices and equivalents thereof.

Directional terms, such as "up", "down", "top" "bottom", "fore", "aft", "lateral", "longitudinal", "radial", "circumferential", etc., are used herein solely for the convenience of the reader in order to aid in the reader's understanding of the illustrated examples. The use of these directional terms does not in any manner limit the described, illustrated, and/or claimed features to a specific direction and/or orientation.

Multiple related items illustrated in the drawings with the same part number which are differentiated by a letter for separate individual instances, may be referred to generally by a distinguishable portion of the full name, and/or by the number alone. For example, if multiple "laterally extending elements" 90A, 90B, 90C, and 90D are illustrated in the drawings, the disclosure may refer to these as "laterally extending elements 90A-90D," or as "laterally extending elements 90," or by a distinguishable portion of the full name such as "elements 90".

The language used in the disclosure are presumed to have only their plain and ordinary meaning, except as explicitly defined below. The words used in the definitions included herein are to only have their plain and ordinary meaning. Such plain and ordinary meaning is inclusive of all consistent dictionary definitions from the most recently published Webster's and Random House dictionaries. As used herein, the following definitions apply to the following terms or to common variations thereof (e.g., singular/plural forms, past/present tenses, etc.):

"about" with reference to numerical values generally refers to plus or minus 10% of the stated value. For example, if the stated value is 4.375, then use of the term "about 4.375" generally means a range between 3.9375 and 4.8125.

"air" as used means atmospheric air or any kind of gas, including pressurized gas.

"air inlet" as used means an opening through which various breathable gases may flow into a component or device.

"air outlet" as used means an opening through which various gases may flow out of a component or device.

"ambient" is the surrounding atmosphere and its conditions. When a concrete pressure is needed for measurement and/or comparison purposes, it is measured at sea level.

"and/or" is inclusive here, meaning "and" as well as "or". For example, "P and/or Q" encompasses, P, Q, and P with Q; and, such "P and/or Q" may include other elements as well.

"compressed breathable gas" is a source of compressed gas, for example oxygen, or air and oxygen, or nitrogen and oxygen, or medical gas, or otherwise breathable by humans and pressurized above ambient. Sources of compressed gas may include that supplied by air pumps, pressurized medical gas tanks, oxygen concentrators or portable air compressors.

"downstream" as used herein means in the direction of the flow of gas through the flow generator from the oxygen source to the patient delivery device.

"external gear" as used herein means a gear with the teeth cut/formed on the outer surface of a cylinder or cone, and the teeth extend away from the center of the gear.

"flow generator" as used herein means any device that provides fluid flow to a breathing circuit of a patient.

"fluid" as used herein means any liquid or gas.

"gas inlet" as used means an opening through which various breathable gases may flow into a component or device.

"gas outlet" as used means an opening through which various gases may flow out of a component or device.

"gear train" as used herein means a set of interconnected gears. Such interconnection may be direct or indirect, such as with intermediate gear(s) and/or gear racks.

"internal gear" as used herein means a gear with the teeth formed on a radially inward facing circumference, or part thereof, of circle.

"multiple" as used herein is synonymous with the term "plurality" and refers to more than one, or by extension, two or more.

"optionally" as used herein means discretionary; not required; possible, but not compulsory; left to personal choice.

"oxygen source" as used herein the source of the oxygen (normally enhanced from ambient, but not normally pure oxygen) being provided into the gas flow path of the flow generator. For example, atmospheric air or oxygen from an artificial source, such as an oxygen tank.

"path" as used herein means a route of flow of gas from the starting point through the flow generator to the patient.

"substantially" generally refers to the degree by which a quantitative representation may vary from a stated reference without resulting in an essential change of the basic function of the subject matter or element modified. The term "substantially" is utilized herein to represent the inherent degree of uncertainty that may be attributed to any quantitative comparison, value, measurement, and/or other representation.

"upstream" as used herein means the opposite of downstream.

The invention claimed is:

1. A valve for use for a respiration system blending at least two gases sources, comprising:
a valve adapted to: (a) be disposed upstream of a patient delivery device selected from the group comprising a mask, mouthpiece, nasal inlet, and combinations thereof, and (b) control at least a portion of a breathable gas source upstream of said patient delivery device and said source comprising both: (i) a first gas source and (ii) a second gas source; said valve comprises:
a rotatable first rotation member, said first rotation member upon rotation causes movement of first gear teeth and a movement of a first valve body providing adjustment of gas flow through a first flow path of said first valve body, wherein said first gear teeth are in an arc around at least an inner portion of the first rotatable member; and
second gear teeth engaging said first gear teeth and movable in response to movement thereof;
a second valve body movable in response to movement of said second gear teeth;
wherein movement of said first rotation member causes simultaneous movement of: (a) said first valve body, and (b) said second valve body providing adjustment of gas flow through a second flow path.

2. The valve of claim 1, wherein said first gas and second gas blend into a common path for breathable gas.

3. The valve of claim 1, wherein said first rotation member is a first rotatable gear.

4. The valve of claim 3, wherein said second gear teeth is in an arc around at least an outer portion of a second rotatable gear.

5. The valve of claim 4, wherein said first rotatable gear is a ring gear with said first gear teeth along an inner portion thereof and engaging said second teeth on an outer portion of said second rotatable gear.

6. The valve of claim 1, wherein said first valve body has an opening of varying cross-sectional area providing a variable first flow rate in response to movement of said first valve body.

7. The valve of claim 1, wherein the second gas source is atmospheric air, wherein the movable second valve body is a rotatable entrainment valve, and wherein in response to rotation of said entrainment valve, the rate of atmospheric air flow through the second flow path is adjusted.

8. The valve of claim 1, in combination with, attached or in a kit, a patient delivery device.

9. A valve for use for a respiration system blending at least two gases sources, comprising:
a valve adapted to: (a) be disposed upstream of a patient delivery device selected from the group comprising a mask, mouthpiece, nasal inlet, and combinations thereof, and (b) control at least a portion of a breathable gas source upstream of said patient delivery device and said source comprising both: (i) a first gas source and (ii) a second gas source; said valve comprises:
a rotatable first rotation member, said first rotation member upon rotation causes movement of first gear teeth and a movement of a first valve body providing adjustment of gas flow through a first flow path of said first valve body; and
second gear teeth engaging said first gear teeth and movable in response to movement thereof;
a second valve body movable in response to movement of said second gear teeth;
wherein movement of said first rotation member causes simultaneous movement of: (a) said first valve body, and (b) said second valve body providing adjustment of gas flow through a second flow path;
wherein said first gear teeth are in an arc around at least a portion of a first rotatable gear wherein said second gear teeth is in an arc around at least an outer portion of a second rotatable gear, and wherein said first rotatable gear is a ring gear with said first gear teeth along an inner portion thereof and engaging said second teeth on an outer portion of said second rotatable gear.

10. A valve for use for a respiration system blending at least two gases sources, comprising:
a valve adapted to: (a) be disposed upstream of a patient delivery device selected from the group comprising a mask, mouthpiece, nasal inlet, and combinations thereof, and (b) control at least a portion of a breathable gas source upstream of said patient delivery device and said source comprising both: (i) a first gas source and (ii) a second gas source; said valve comprises:
a rotatable first rotation member, said first rotation member upon rotation causes movement of first gear teeth and a movement of a first valve body providing adjustment of gas flow through a first flow path of said first valve body; and
second gear teeth engaging said first gear teeth and movable in response to movement thereof;
a second valve body movable in response to movement of said second gear teeth;
wherein movement of said first rotation member causes simultaneous movement of: (a) said first valve body, and (b) said second valve body providing adjustment of gas flow through a second flow path, and wherein said first valve body has at least two distinct and different sized apertures providing two different first flow rates.

11. The valve of claim 10, wherein said second valve body has at least two distinct and different sized apertures providing two different second flow rates.

12. The valve of claim 11, wherein said simultaneous movement of said valve bodies cause said first flow rate and said second flow rate to change together simultaneously.

13. A valve for use for a respiration system blending at least two gases sources, comprising:
a valve adapted to: (a) be disposed upstream of a patient delivery device selected from the group comprising a mask, mouthpiece, nasal inlet, and combinations thereof, and (b) control at least a portion of a breathable gas source upstream of said patient delivery device and said source comprising both: (i) a first gas source and (ii) a second gas source; said valve comprises:
a rotatable first rotation member, said first rotation member upon rotation causes movement of first gear teeth and a movement of a first valve body providing adjustment of gas flow through a first flow path of said first valve body; and
second gear teeth engaging said first gear teeth and movable in response to movement thereof;
a second valve body movable in response to movement of said second gear teeth;
wherein movement of said first rotation member causes simultaneous movement of: (a) said first valve body, and (b) said second valve body providing adjustment of gas flow through a second flow path, and wherein said first valve body and second valve body have the same axis of rotation.

14. A valve and flow generator combination device for use with a compressed breathable gas source, comprising:
a gas flow path adapted to deliver gas from the compressed breathable gas source to a patient delivery device; and
a gas connector operably attached to the compressed breathable gas source;
a valve body operably located downstream of the gas connector and configured to selectively control a gas flow rate through the gas path downstream of the valve body comprising at least a first aperture and a second aperture, wherein the valve body comprises: a gear including an inner gear engaging with an inner surface of an outer ring gear;
wherein the valve body is selectively movable between at least a first position placing the first aperture within the gas flow path and a second position placing the second aperture within the gas flow path; and
wherein in the first position the gas flow rate is a first flow rate, in the second position the gas flow rate is a second flow rate lower than the first flow rate.

15. The device of claim 14, wherein the valve body is a rotary valve.

16. The device of claim 14, wherein at least a portion of an outer surface of the inner gear includes teeth, and wherein the teeth on the inner gear engage with teeth extending around at least a portion of the inner surface of the outer ring gear.

17. The device of claim 14, wherein the valve body includes an axis, wherein the axis of the valve body extends parallel to an axis of the gas flow path.

18. The device of claim 14, wherein the valve body is selectively movable between the first position, the second position and a third position, and wherein in the third position the gas flow rate is a third flow rate lower than the second flow rate.

19. The device of claim 18, wherein the first flow rate is about 20-30 L/min, the second flow rate is about 15-25 L/min and the third flow rate is about 0-15 L/min, and, further comprising:
an entrainment valve configured to selectively control the amount of atmosphere entrained within the gas flow path;
wherein the atmosphere entrainment valve is movable between at least three different positions; and
wherein in each position different levels of atmosphere are entrained into the gas flow path.

20. The device of claim 14, in combination with, also comprising attached to or in a kit with, a patient delivery device.

* * * * *